(12) United States Patent
Lambourne (10) Patent No.: US 8,823,924 B2
(45) Date of Patent: Sep. 2, 2014

(54) COMBINED MEASUREMENT OF NEUTRON FLUENCE WITH TEMPERATURE AND/OR PRESSURE

(75) Inventor: Alexis Lambourne, Belper (GB)

(73) Assignee: Rolls-Royce PLC, London (GB)

(*) Notice: Subject to any disclaimer, the term of this patent is extended or adjusted under 35 U.S.C. 154(b) by 0 days.

(21) Appl. No.: 13/699,672

(22) PCT Filed: May 13, 2011

(86) PCT No.: PCT/EP2011/057745
§ 371 (c)(1),
(2), (4) Date: Nov. 23, 2012

(87) PCT Pub. No.: WO2011/154216
PCT Pub. Date: Dec. 15, 2011

(65) Prior Publication Data
US 2013/0083314 A1  Apr. 4, 2013

(30) Foreign Application Priority Data
Jun. 9, 2010  (GB) .................................. 1009640.2

(51) Int. Cl.
| | | |
|---|---|---|
| G01N 21/00 | (2006.01) | |
| G01D 21/02 | (2006.01) | |
| H01J 37/32 | (2006.01) | |
| G01D 5/26 | (2006.01) | |
| G01D 5/34 | (2006.01) | |
| G21C 17/10 | (2006.01) | |
| G01N 21/64 | (2006.01) | |

(52) U.S. Cl.
CPC .......... *H01J 37/32935* (2013.01); *G01N 21/64* (2013.01); *G01D 21/02* (2013.01); *G01D 5/266* (2013.01); *G01D 5/34* (2013.01); *G21C 17/10* (2013.01); *G01D 5/268* (2013.01)
USPC ........................................................ 356/72

(58) Field of Classification Search
CPC ... H01J 37/32935; G01N 21/64; G01N 21/68; G01N 2015/1037; G01J 3/02

USPC ....... 356/519, 72; 355/55; 250/83.1; 376/247
See application file for complete search history.

(56) References Cited

U.S. PATENT DOCUMENTS

| 3,588,505 A | * | 6/1971 | Ralph ........................... 376/153 |
| 2008/0079920 A1 | * | 4/2008 | Hommen et al. ............... 355/55 |

(Continued)

FOREIGN PATENT DOCUMENTS

| DE | 196 50 073 A1 | 6/1998 |
| WO | WO 2005/098385 A1 | 10/2005 |

OTHER PUBLICATIONS

Pells et al., "Use of Sapphire as a Neutron Damage Monitor for Pressure Vessel Steels," Reactor Dosimetry: Methods, Applications, and Standardizations, ASTM STP vol. 1001, 1989, pp. 659-669.

(Continued)

*Primary Examiner* — Tarifur Chowdhury
*Assistant Examiner* — Md Rahman
(74) *Attorney, Agent, or Firm* — Oliff PLC (57) ABSTRACT

A sensor is provided that includes a first optical body having at opposing, spaced sides an incident surface and a reflecting surface. The sensor includes an optical pathway for carrying incident light to the incident surface. The first optical body acts as a Fabry-Pérot etalon, such that a portion of the incident light passes through the incident surface, reflects from the reflecting surface, and then returns along the optical pathway. The first optical body is formed of a material whose optical absorbance increases depending on the neutron fluence experienced by the material, such that a corresponding characteristic attenuation is produced in the reflected light returned along the optical pathway depending on the neutron fluence experienced by the first optical body. The sensor may measure pressure in combination with the measurement of temperature and neutron fluence, and a further sensor is provided for combined measurement of pressure and neutron fluence.

9 Claims, 10 Drawing Sheets

(56) References Cited

U.S. PATENT DOCUMENTS

2010/0128284 A1* 5/2010 Riza et al. .................. 356/519
2013/0170596 A1* 7/2013 Ginsberg et al. ............ 376/247

OTHER PUBLICATIONS

Mar. 15, 2012 International Search Report issued in International Application No. PCT/EP2011/057745.

Mar. 15, 2012 Written Opinion of the International Searching Authority issued in International Application No. PCT/EP2011/057745.

"Cobalt-60;" Wikipedia: The Free Encyclopedia; Web; Accessed Dec. 19, 2012; http://en.wikipedia.org/wiki/Cobalt_60.

Hernandez; "Fabry-Perot Interferometers;" Cambridge Studies in Modern Optics; 1986; pp. 91-107; pp. 114-117; and pp. 259-260.

Avery et al.; "Neutron dosimetry for advanced pressurized water reactors;" Nucl. Energy; 1994; vol. 33, No. 6; pp. 359-373.

* cited by examiner

| Type | Detector and Reaction | Half-life of Product | Effective Energy Threshold (MeV) |
|---|---|---|---|
| Thermal | $^{59}Co(n,\gamma)^{60}Co$ | 5.27y | Thermal |
| | $^{58}Fe(n,\gamma)^{59}Fe$ | 44.5d | Thermal |
| | $^{63}Cu(n,\gamma)^{64}Cu$ | 12.70h | Thermal |
| Fission | $^{237}Np(n,f)FP$ | 12d-30y | 0.67 |
| | $^{238}U(n,f)FP$ | 12d-30y | 1.51 |
| | $^{232}Th(n,f)FP$ | 12d-30y | 1.52 |
| Threshold | $^{93}Nb(n,n')^{93m}Nb$ | 16-13y | 0.50 |
| | $^{115}In(n,n')^{115m}In$ | 4.49h | 0.95 |
| | $^{47}Ti(n,p)^{47}Sc$ | 3.35d | 1.90 |
| | $^{58}Ni(n,p)^{58}Co$ | 70.8d | 2.10 |
| | $^{54}Fe(n,p)^{54}Mn$ | 312.1d | 2.50 |
| | $^{46}Ti(n,p)^{46}Sc$ | 83.8d | 3.90 |
| | $^{48}Ti(n,p)^{48}Sc$ | 43.7h | 5.70 |
| | $^{63}Cu(n,\alpha)^{60}Co$ | 5.27y | 6.10 |
| | $^{127}Al(n,\alpha)^{24}Na$ | 14.96h | 6.50 |

Fig.4

Fig.5(a)
Sensor Arrangement

Fig.5(b)
Temperature Measurement

Fig.5(c)
Pressure Measurement

Fig.5(d)
Pressure Measurement

Fig.12
Neutron Measurement

COMBINED MEASUREMENT OF NEUTRON FLUENCE WITH TEMPERATURE AND/OR PRESSURE

FIELD OF THE INVENTION

The present invention relates to a sensor for combined measurement of neutron fluence with temperature and/or pressure.

BACKGROUND OF THE INVENTION

Nuclear reactors require measurement of the neutron fluence or neutron dose (i.e. the number of impinging neutrons per unit area).

Figure 1:
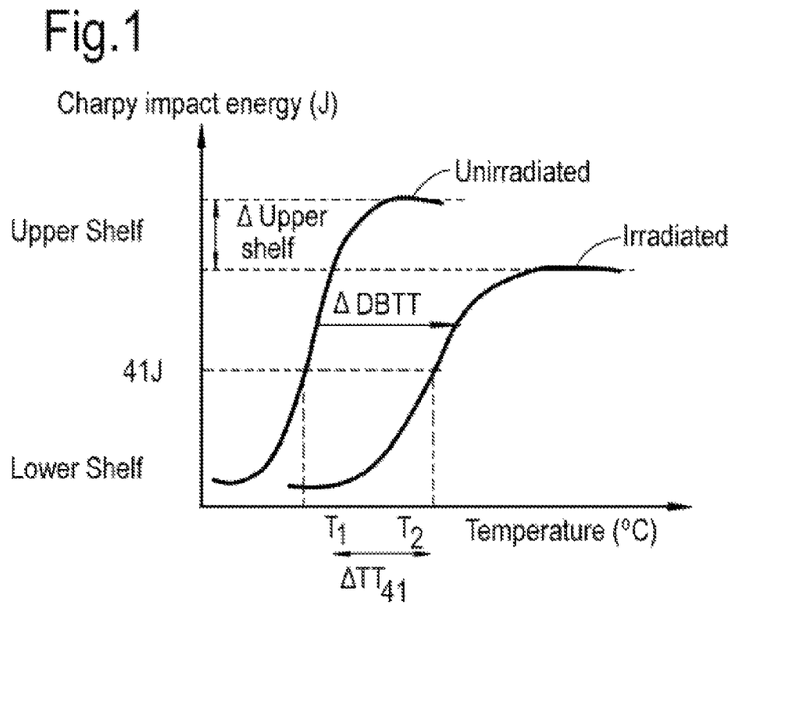
FIG. 1 shows a graph of Charpy impact energy against temperature for un-irradiated and irradiated pressure vessel steel.

Neutron fluence is important as neutrons straying from the reactor core cause damage to the materials that make up components of the reactor, such as the reactor pressure vessel (RPV). This neutron damage leads to a progressive undermining of the properties of the material, i.e. typically increased hardness, reduced fracture toughness, and reduced impact strength. FIG. 1 shows a graph of Charpy impact energy against temperature for un-irradiated and irradiated pressure vessel steel, and shows the reduced upper-shelf toughness and the shift in the ductile to brittle transition temperature ($\Delta$DBTT) at an impact energy of 41 Joules ($\Delta$TT41).

This "irradiation shift" must be understood if the behaviour of the materials comprising the nuclear reactor are to be effectively predicted. Predictive models are used to determine the irradiation shift behaviour and calculate remnant service life of the reactor. Critical to these models is a good understanding of the neutron fluence experienced by the reactor materials.

Figure 2:
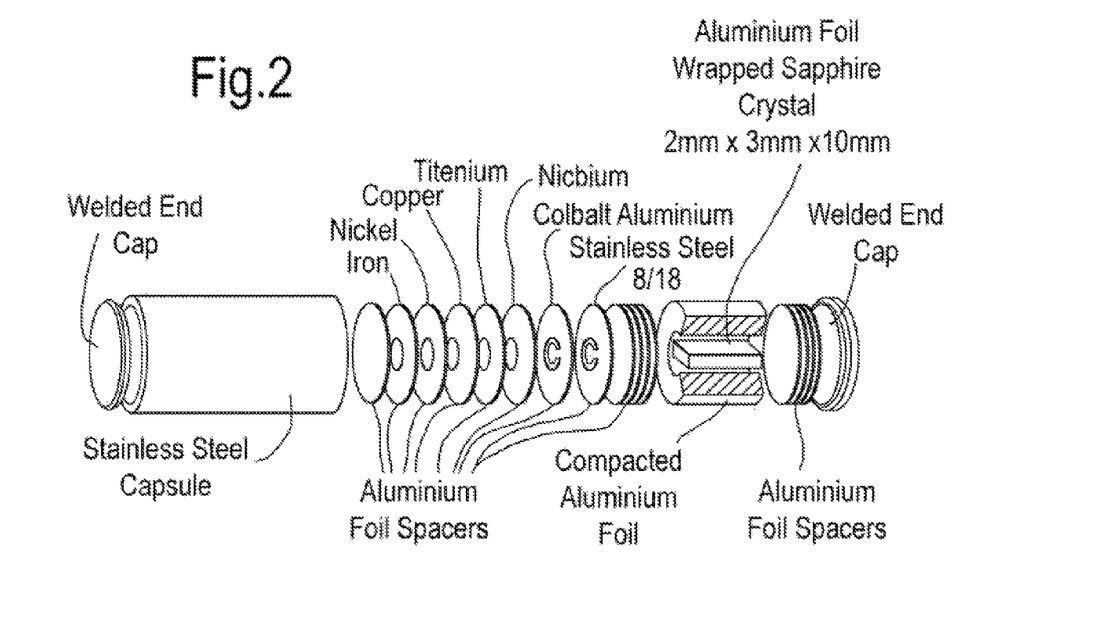
FIG. 2 shows a schematic exploded view of a conventional dosimetery activation monitor.

Fluence is measured using dosimetry. Conventional dosimetry is based on activation monitors. These are capsules containing foils of different metals which undergo an activation/reaction when neutrons of different energies impinge on them. FIG. 2 (taken from Pells, Fudge, Murphy and Watt, *Use of Sapphire as a Neutron Damage Monitor for pressure vessel steels*, ASTM STP 1001, p. 659-669, 1989) shows a schematic exploded view of such a monitor.

The dosimetry capsule is loaded into the reactor and used to measure the neutron fluence experienced by certain reactor components (e.g. the RPV). The reactions given in the table of FIG. 3 (taken from the Pells, Fudge, Murphy and Watt reference) indicate the reaction that different metals undergo and which neutron energies they represent.

There are, however, disadvantages with conventional dosimetry capsules. Firstly, the capsule is sealed within the reactor and can only be analysed and interrogated when the reactor is shut down, de-pressurised and opened for maintenance or re-fuelling. This means that it may be 10 to 20 years after reactor commissioning before the first measurement of neutron fluence experienced by critical components such as the RPV can be obtained. In the total life of a nuclear reactor it may only be possible to extract dosimetry capsules 2 or 3 times. This leads to a sparse database of neutron fluence information on which to base materials irradiation shift predictions. As a consequence, critical materials lifing decisions may be made with incomplete data and overly conservative materials models.

Figure 3:
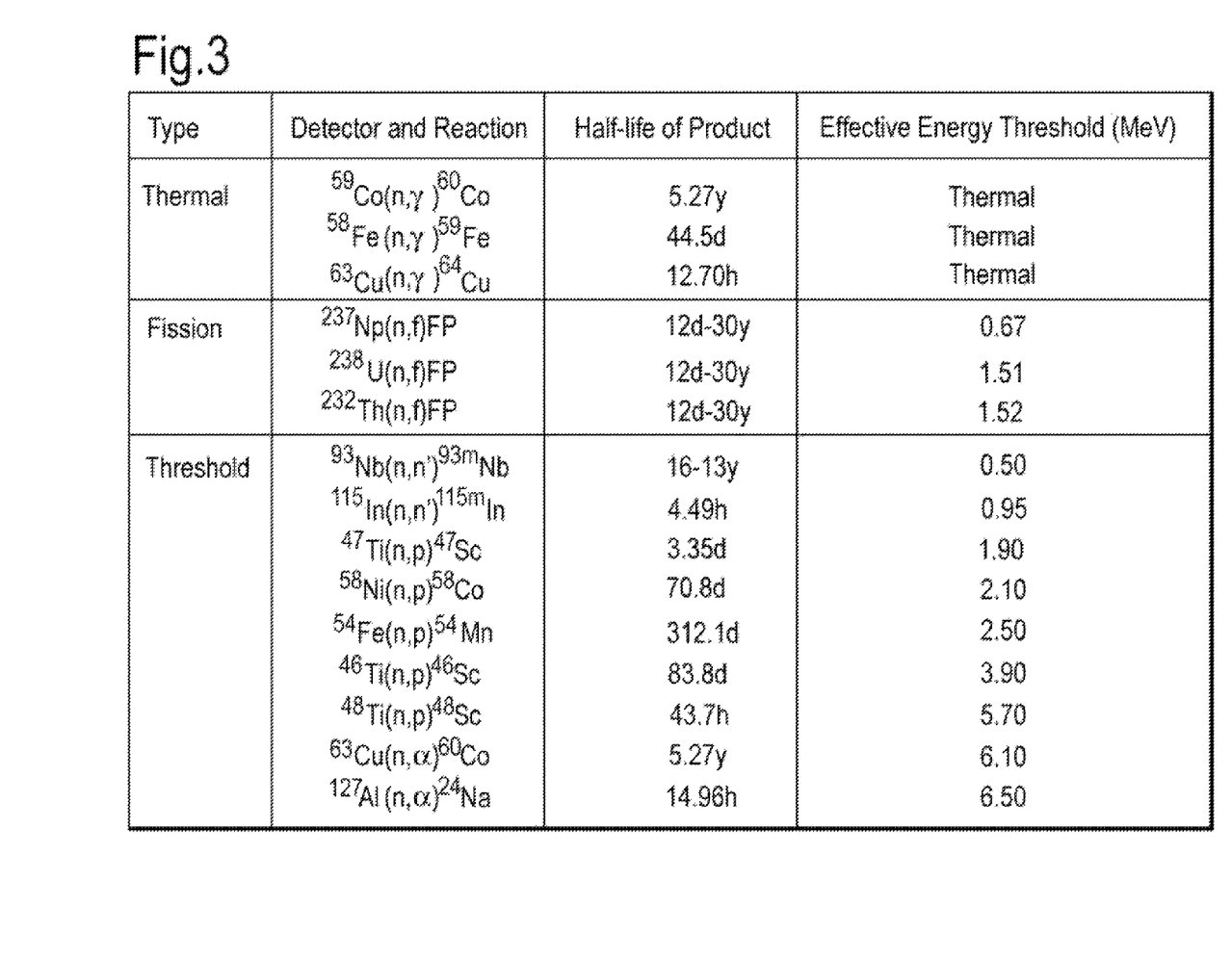
FIG. 3 shows a table of reactions, half lives and threshold energies for different dosimetry foils.
Figure 4:
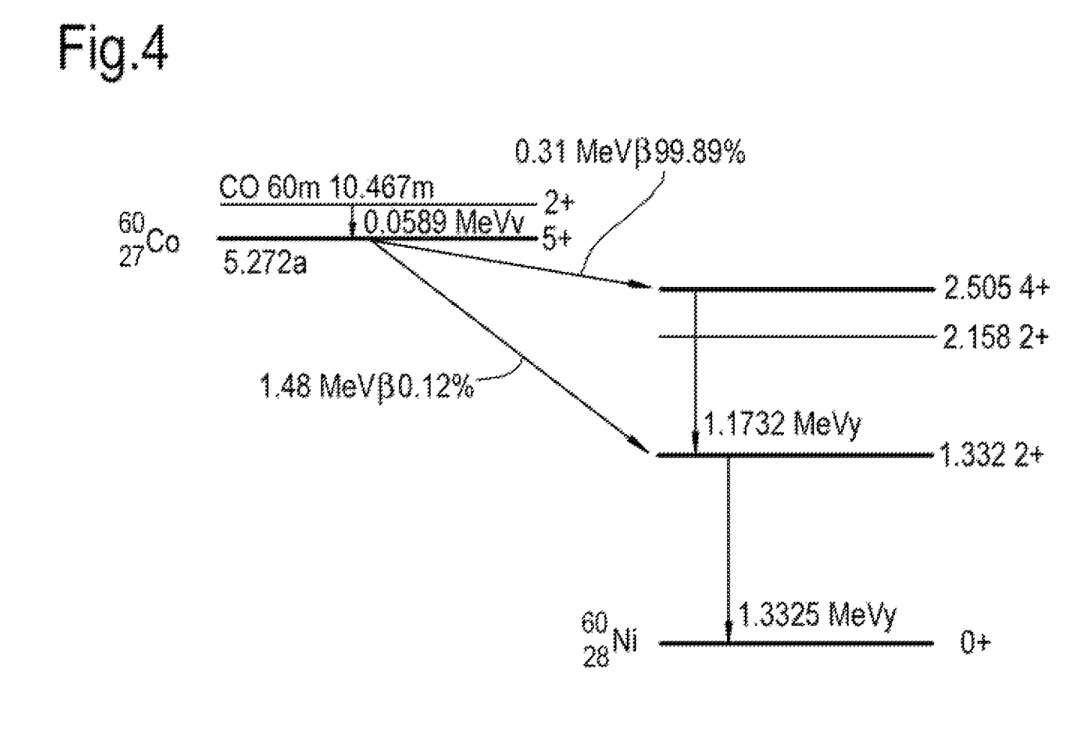
FIG. 4 shows a decay scheme for $Co^{60}$.

Secondly, as the table of FIG. 3 indicates, conventional dosimetry involves the activation of the metal foils. For example, $Co^{60}$ is produced artificially by neutron activation of elemental foil of $Co^{59}$ in the dosimetry capsule. $Co^{60}$ then decays by negative beta decay to the stable isotope nickel-60 ($Ni^{60}$), the activated Ni-atom emitting two gamma rays with energies of 1.17 and 1.33 MeV as indicated by the decay scheme shown in FIG. 4 (taken from http://en.wikipedia.org/wiki/Cobalt_60). However, the half-life of $Co^{60}$ is 5.27 years, meaning that it remains radioactive during the period in which it must be measured and studied. Indeed, all dosimetry foils become radioactive in order to be measured. This makes it necessary to take many precautions while handling and studying dosimetry foils. For example, measurements must be performed remotely, in hot-cell facilities, which significantly increase the cost and complexity of the dosimetry interpretation process. An additional complication is that the half-lives of the dosimetry foils are different, such that the radiation record changes with time and this must be accounted for when calculating neutron fluence.

The sparse and discontinuous neutron fluence data available from dosimetry capsules make it necessary to use a complex process to calculate fluence. This process incorporates dosimetry data, physics-based predictions, and spectrum unfolding algorithms, as well as materials testing, reactor data, historical databases and past experience.

Thus, it would be desirable to provide a neutron fluence measuring device which avoids or overcomes at least some of the problems associated with dosimetry capsules.

SUMMARY OF THE INVENTION

The present invention is at least partly based on the realisation that Fabry-Pérot etalons and interferometers, which are conventionally used to measure temperature and pressure in harsh environments, can be adapted to also measure neutron fluence.

Accordingly, a first aspect of the present invention provides a sensor for combined measurement of temperature and neutron fluence, the sensor comprising:

a first optical body having at opposing, spaced sides an incident surface and a reflecting surface, and an optical pathway for carrying incident light to the incident surface, the first optical body acting as a Fabry-Pérot etalon, such that a portion of the incident light passes through the incident surface, reflects from the reflecting surface, and then returns along the optical pathway;

wherein:

varying the temperature of the first optical body leads to changes in the spacing between the incident and reflecting surfaces due to thermal expansion or contraction of the first optical body, such that corresponding temperature-sensitive characteristic changes are produced in the reflected light returned along the optical pathway, and the first optical body is formed of a material whose optical absorbance increases depending on the neutron fluence experienced by the material, such that a corresponding characteristic attenuation is produced in the reflected light returned along the optical pathway depending on the neutron fluence experienced by the first optical body.

Preferably, the sensor is also for measurement of pressure in combination with measurement of temperature and neutron fluence, the sensor further comprising:

a Fabry-Pérot interferometer having a cavity bounded on opposing sides by the mirrored surface of the first optical body and a higher finesse mirrored surface of a second optical body, wherein a portion of the incident light passes through the first optical body, enters the cavity, reflects from the higher finesse mirrored surface, and then returns along the optical pathway;

wherein:

at least one of the optical bodies is arranged such that it deforms under the influence of external pressure to vary the distance between the mirrored surfaces on the opposing sides of the cavity, leading to corresponding pressure-sensitive characteristic changes in the reflected light returned along the optical pathway.

A second aspect of the present invention provides a sensor for combined measurement of pressure and neutron fluence, the sensor comprising:

a Fabry-Pérot interferometer having a cavity bounded on opposing sides by the mirrored surface of a first optical body and a higher finesse mirrored surface of a second optical body, and an optical pathway for carrying incident light to an incident surface of the first optical body, wherein a portion of the incident light passes through the first optical body, enters the cavity, reflects from the higher finesse mirrored surface, and then returns along the optical pathway;

wherein:

at least one of the optical bodies is arranged such that it deforms under the influence of external pressure to vary the distance between the mirrored surfaces on the opposing sides of the cavity, leading to corresponding pressure-sensitive characteristic changes in the reflected light returned along the optical pathway, and the first optical body, and/or the second optical body, is formed of a material whose optical absorbance increases depending on the neutron fluence experienced by the material, such that a corresponding characteristic attenuation is produced in the reflected light returned along the optical pathway depending on the neutron fluence experienced by the first and/or the second optical body. Preferably, at least the first optical body is formed of the material whose optical absorbance increases depending on the neutron fluence experienced by the material.

Thus a single sensor can measure the neutron fluence, and at least one and preferably two other parameters which are needed for the safe operation of a nuclear reactor. The sensor avoids many of the operational disadvantages associated with dosimetry capsules. In particular, it allows large and reliable neutron fluence datasets to be obtained.

The sensor of the first or second aspect may have any one or, to the extent that they are compatible, any combination of the following optional features.

When the sensor measures pressure, preferably the second optical body (and more preferably only the second optical body) is arranged such that it deforms under the influence of external pressure to vary the distance between the mirrored surfaces on the opposing sides of the cavity.

Preferably, the second optical body is also formed of a material whose optical absorbance increases depending on the neutron fluence experienced by the material.

Typically, the optical pathway is a fibre optic cable.

Preferably, the material whose optical absorbance increases depending on the neutron fluence experienced by the material is sapphire. Advantageously, sapphire exhibits an optical absorbance change which is consistent across a range of different irradiation temperatures, reactor types and neutron spectrums. However, other possible materials include other optically transparent transition metal oxides, or (particularly for low temperature applications) doped and/or dyed polymers.

The sensor may further have a source of the incident light, the source being arranged to transmit the incident light along the optical pathway to the interferometer. For example, the source can be a laser or an LED, which provide incident light of a specific wavelength. Preferably, the source produces incident light having a wavelength in the range from 380 to 450 nm. Sapphire exhibits large differences between the irradiated and un-irradiated optical absorptions at these wavelengths, improving sensor sensitivity. Also a plateau in the optical absorption of irradiated sapphire in this range helps to reduce measurement uncertainties.

The sensor may further have a detector arranged to detect the reflected light returned along the optical pathway. For example, the detector may comprise a photo-multiplier.

The sensor may further have a processor unit operatively connected to the detector for determining the neutron fluence experienced by the interferometer from the characteristic attenuation. The processor unit preferably further determines the temperature and/or external pressure from the temperature-sensitive and/or the pressure-sensitive characteristic change. The sensor may further have a display and/or a memory device for respectively displaying and/or storing the determined neutron fluence. The display and/or the memory device preferably also respectively display and/or store the determined temperature and/or external pressure.

A third aspect of the present invention provides a nuclear reactor pressure vessel fitted with one or more sensors according to the first or second aspect.

A fourth aspect of the present invention provides the use of a sensor according to the first or second aspect for measuring neutron fluence.

BRIEF DESCRIPTION OF THE DRAWINGS

Embodiments of the invention will now be described by way of example with reference to the accompanying drawings in which.

DETAILED DESCRIPTION

A Fabry-Pérot interferometer consists of two parallel flat semi-transparent mirrors separated by a fixed distance. Light that enters the cavity between the mirrors undergoes multiple reflections and the interference of the light emerging from the interferometer during each bounce causes a modulation in the transmitted and reflected beams. The transmission spectrum of the interferometer has a series of peaks spaced by the free spectral range. The width of each transmission peak decreases for higher finesse (reflectivity) mirrors, the finesse being defined as the ratio of the free spectral range to the full width half maximum of the transmission peaks. A Fabry-Pérot etalon is a similar device in which the reflections are between spaced, opposing mirrored surfaces of an optical body. Further information on Fabry-Pérot interferometers can be found in G. Hernandez (1986), *Fabry-Pérot Interferometers: Cambridge Studies in Modern Optics* 3, Cambridge University Press.

It is possible to measure concurrently temperature (T) and pressure (P) using a Fabry-Perot etalon and a Fabry-Pérot interferometer in series. Combined temperature and pressure sensors based on this technology are commercially available, for example the Wave-Phire™ range of sensors from Oxsensis Ltd.

Figure 5A:
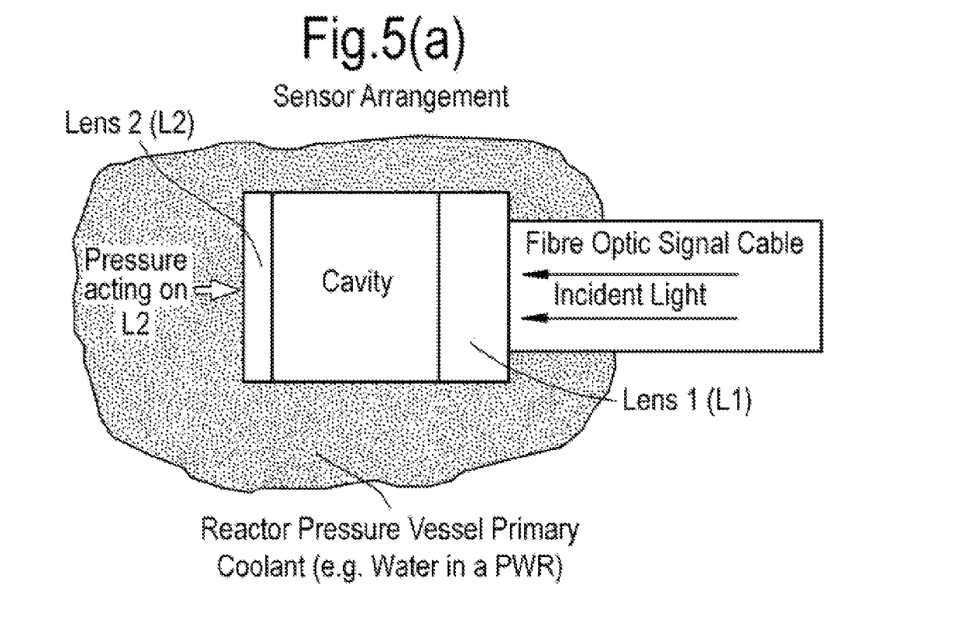
FIGS. 5(a) to (d) show schematically the general arrangement and mode of operation of a combined temperature and pressure sensor.

FIGS. 5(a) to (d) show schematically the general arrangement and mode of operation of a combined temperature and pressure sensor. As shown in FIG. 5(a), incident light from a fibre optic signal cable is incident on a surface of a first optical body, or lens, L1 having a known coefficient of thermal expansion (CTE). On an opposing surface the lens L1 has a low finesse (i.e. part silvered) mirrored surface. Some of the incident light is reflected from the low finesse mirrored surface, but some passes through to cross a cavity and arrive at a high finesse mirrored surface of a second optical body, or lens, L2.

Figure 5B:
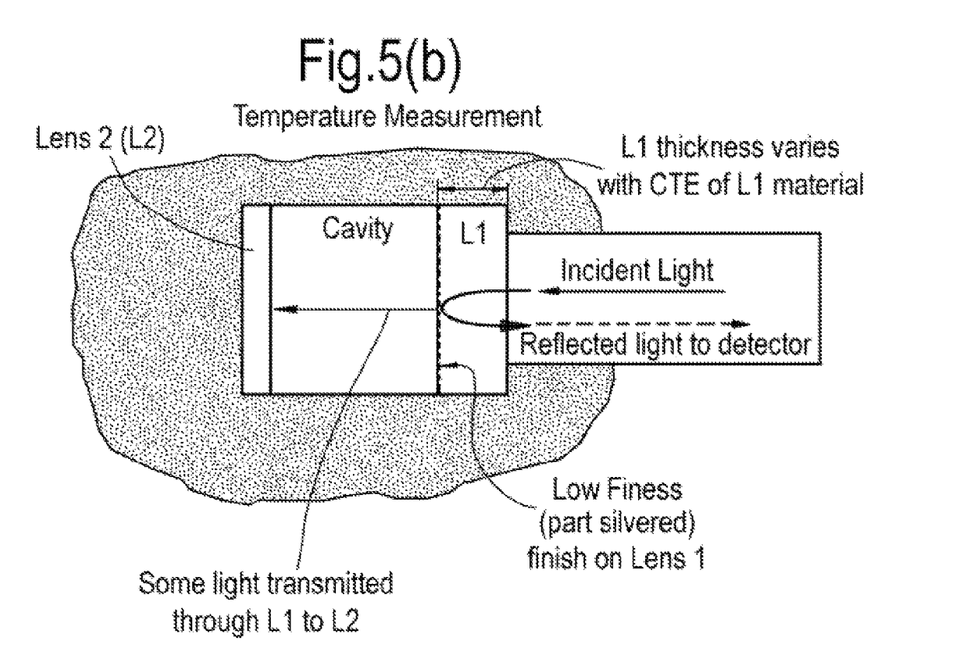

As shown in FIG. 5(b), the lens LI acts as a Fabry-Pérot etalon, with the light reflected from the low finesse mirrored surface returning along the fibre optic signal cable and producing signal peaks whose spacing is characteristic of the thickness of the lens LI. As the thickness of the lens LI varies in a known way with temperature, changes to the spacing of these peaks provides a measure of the temperature at the sensor.

Figure 5C:
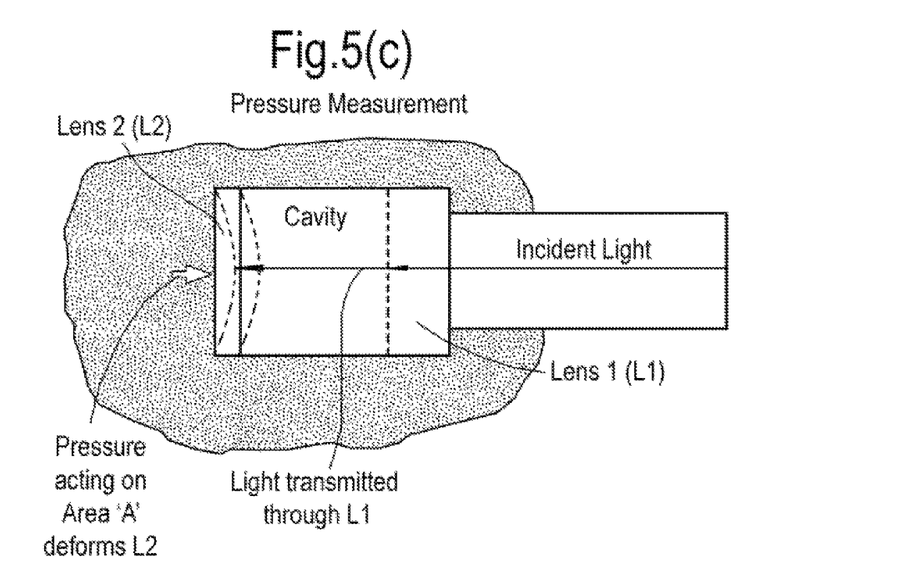
Figure 5D:
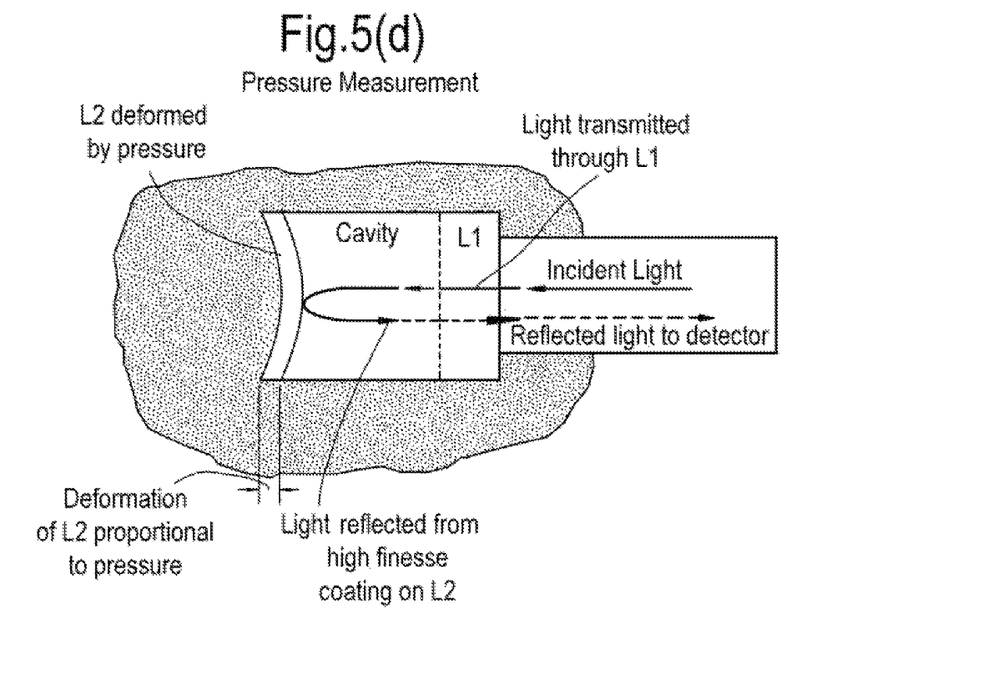

As shown in FIG. 5(c), the external pressure acting on the lens L2 exerts a force on the known area of the lens L2, causing the lens L2 to deflect. With knowledge of the Young's Modulus (stress-strain) behaviour of the material of the lens L2 and the magnitude of the deflection of the lens L2 into the cavity, it possible to work out the force acting on the area of the lens L2 and thereby to calculate the external pressure on the lens L2. However, as shown in FIG. 5(d), the lens LI acts as a Fabry-Pérot interferometer, a portion of the incident light passing through the lens L1, entering the cavity and reflecting off the high finesse mirrored surface of the lens L2. This produces a further signal in the reflected light returning along the fibre optic signal cable which is characteristic of the length of the cavity. Thus changes to the further signal provide a measure of the length of the cavity, from which the external pressure can be calculated.

Figure 6:
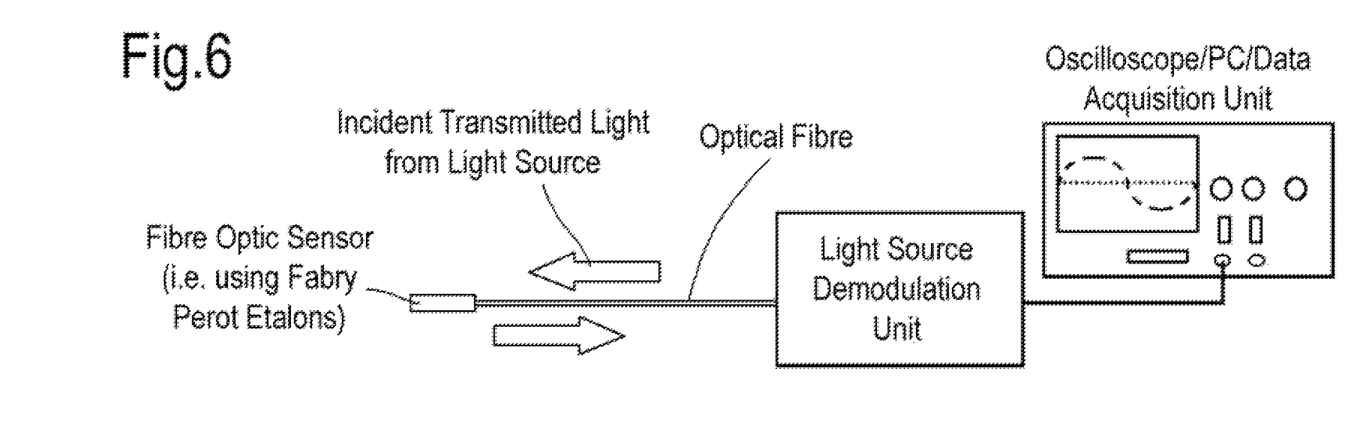
FIG. 6 shows a general arrangement of the sensor of FIGS. 5(a) to (d)
Figure 7:
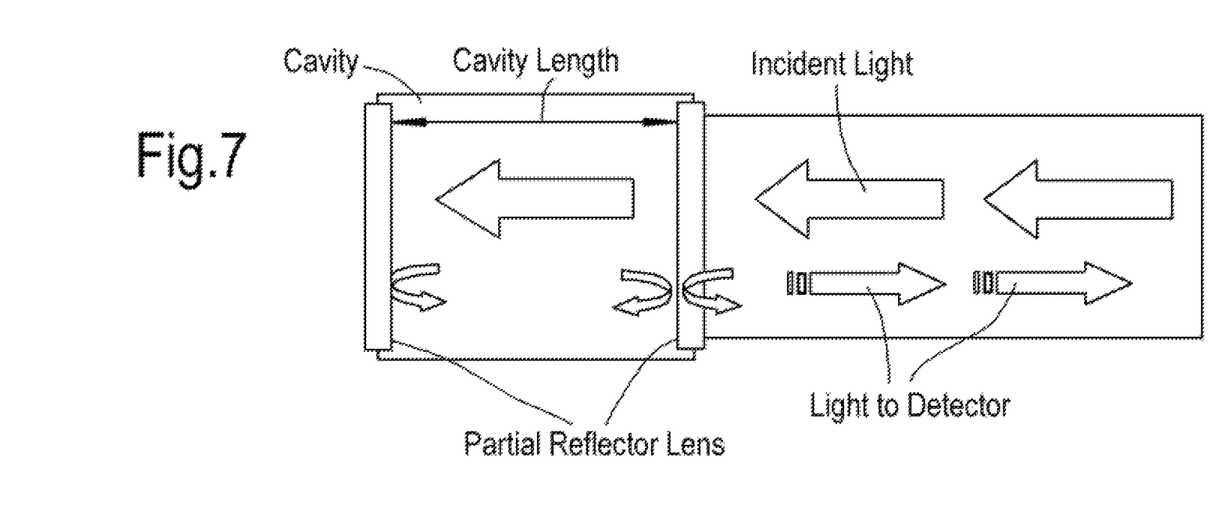
FIG. 7 shows schematically the combined reflected signals from lenses L1 and L2 of the sensor of FIGS. 5(a) to (d)
Figure 8:
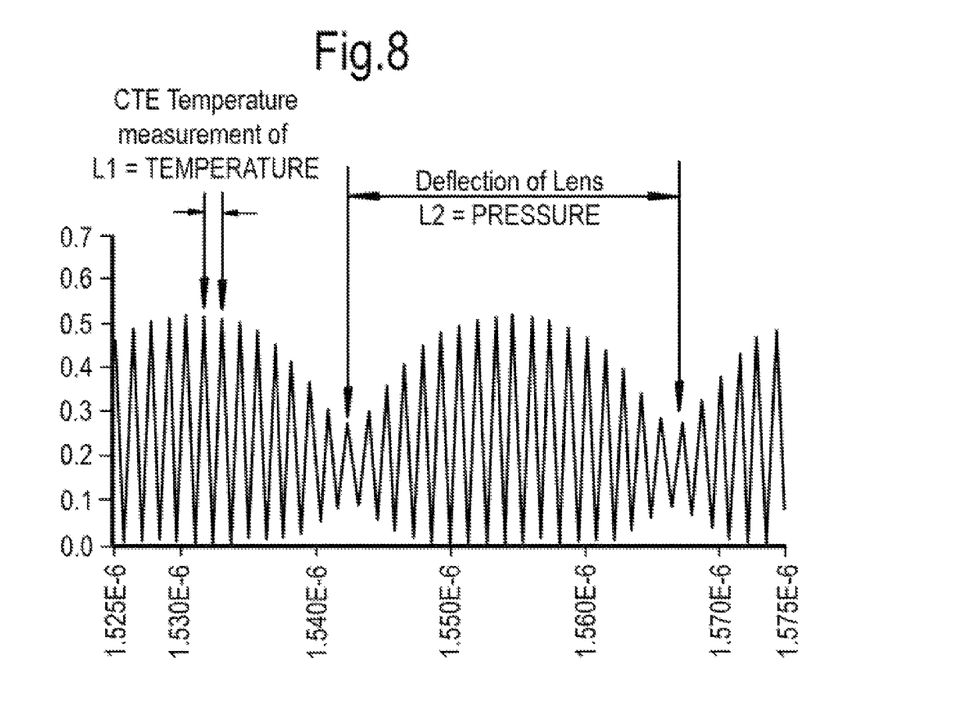
FIG. 8 shows an example of the return signal from the sensor of FIGS. 5(a) to (d) after processing and display on an oscilliscope.

FIG. 6 shows a general arrangement of the sensor. The light source demodulation unit at the end of the optical fibre typically comprises a photomultiplier. FIG. 7 shows schematically the combined reflected signals from lenses L1 and L2, and FIG. 8 shows an example of the return signal after processing and display on an oscilliscope. In FIG. 8, the distance between peaks represents the thickness of the lens L1 and therefore measures temperature, while the period of the wave envelope formed by multiple temperature peaks represents the length of the cavity and therefore measures the external pressure.

Figure 9:
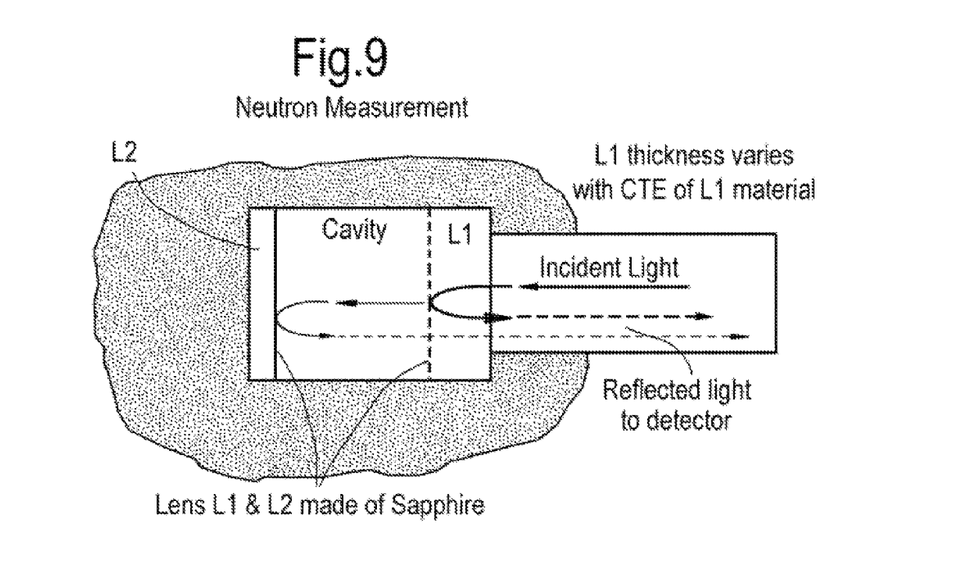
FIG. 9 shows schematically the general arrangement and mode of operation of a combined temperature, pressure and neutron fluence sensor.

FIG. 9 shows schematically the general arrangement and mode of operation of a combined temperature, pressure and neutron fluence sensor. The arrangement of the sensor and the measurement of temperature and pressure using the sensor are similar to the arrangement and measurement described above in relation to the sensor of FIGS. 5(a) to (d). However, in the neutron fluence sensor, the lens L1 and L2 are made of sapphire.

The performance of the sensor makes use of the way that neutrons interact with the crystal lattice of sapphire such that the optical absorbance of sapphire increases depending on the neutron fluence experienced by the sapphire. To understand this interaction it is helpful to consider the process as a series of steps:

1. A neutron exits the core of the reactor, and strikes an atom in the sapphire lattice.

2. The atom struck by the neutron is the Primary Knock-on Atom (PKA). This is propelled through the sapphire lattice causing damage as it travels and progressively losing energy as it travels. The damage is referred to as a displacement cascade.

3. The displacement cascade is inherently unstable and will collapse to restore the low energy equilibrium of the crystalline lattice.

Figure 10:
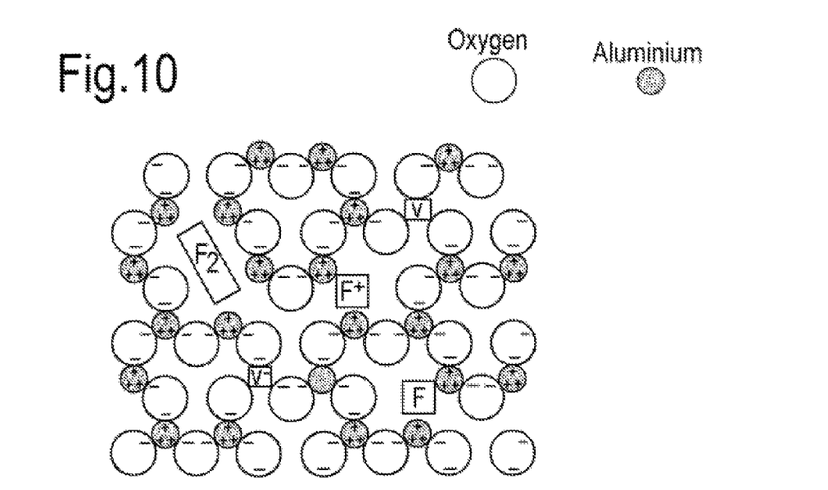
FIG. 10 illustrates common F, F+, F2, V and V− defects in a sapphire lattice.

4. The collapse and "repair" of the crystal lattice is incomplete and some point defect damage remains after cascade collapse. Point defect damage is in the form of interstitials (atoms in the wrong place in the crystal lattice) and vacancies (holes left in the lattice). In sapphire there are two classifications of vacancy, V centres and F centres. These in turn can be designated F1, F2, etc. according to how many atoms are "missing" from the lattice. Common F, F+, F2, V and V− defects in a sapphire lattice are illustrated in FIG. 10 (taken from Avery, Little and Pells, *Neutron dosimetry for advanced pressurized water reactors*, Nuclear Energy, (1994), No 6, December, p. 359-373). Further information can be found in the Pells, Fudge, Murphy and Watt reference.

Figure 11:
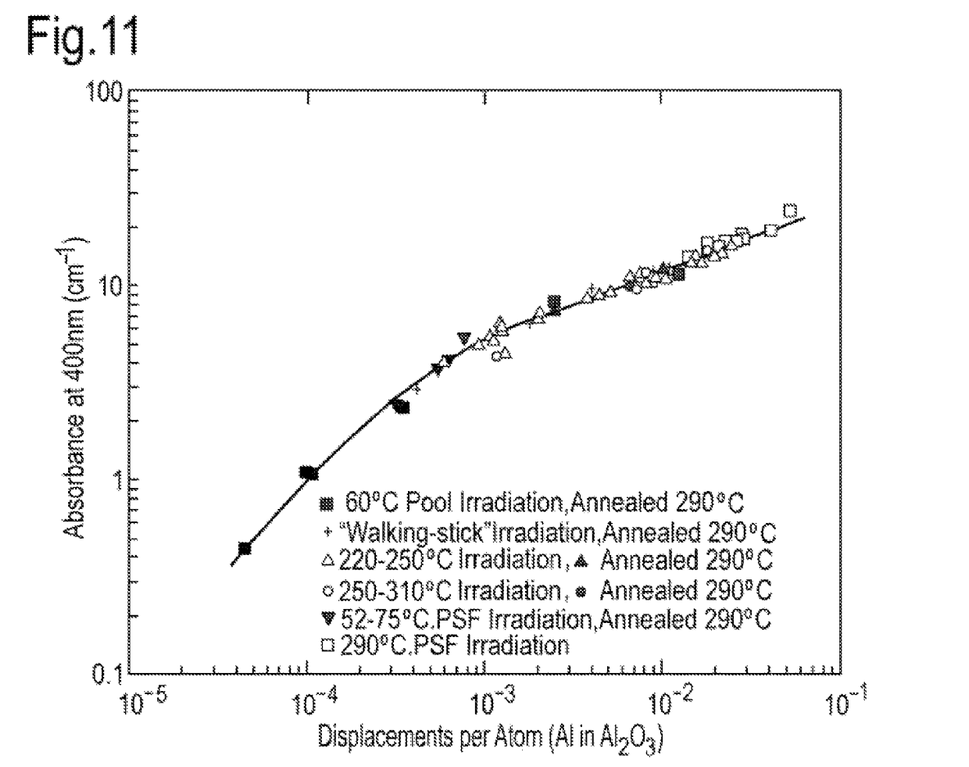
FIG. 11 shows a graph of sapphire optical absorbance at 400 nm against neutron fluence.

The presence of these defects in an optically transparent material like sapphire causes scattering of light, and with increasing defect density the material becomes increasingly opaque. This is illustrated in FIG. 11 which shows a graph from the Pells, Fudge, Murphy and Watt reference of sapphire optical absorbance at 400 nm against neutron fluence. Advantageously, the graph shows that this optical absorbance change is consistent across a range of different irradiation temperatures, reactor types and neutron spectrums.

Sapphire has thus been shown to be an appropriate dosimetery material in temperatures up to 500° C. and for neutron energies of 1 KeV to 2 MeV, which encompasses the thermal and fast neutron spectrum of interest for RPV irradiation shift. The temperature range is also appropriate to next generation PWR and BWR (boiling water reactor) plant designs. However, other possible materials for the lenses L1 and L2 include other optically transparent transition metal oxides, or (particularly for low temperature applications) doped and/or dyed polymers.

Figure 12:
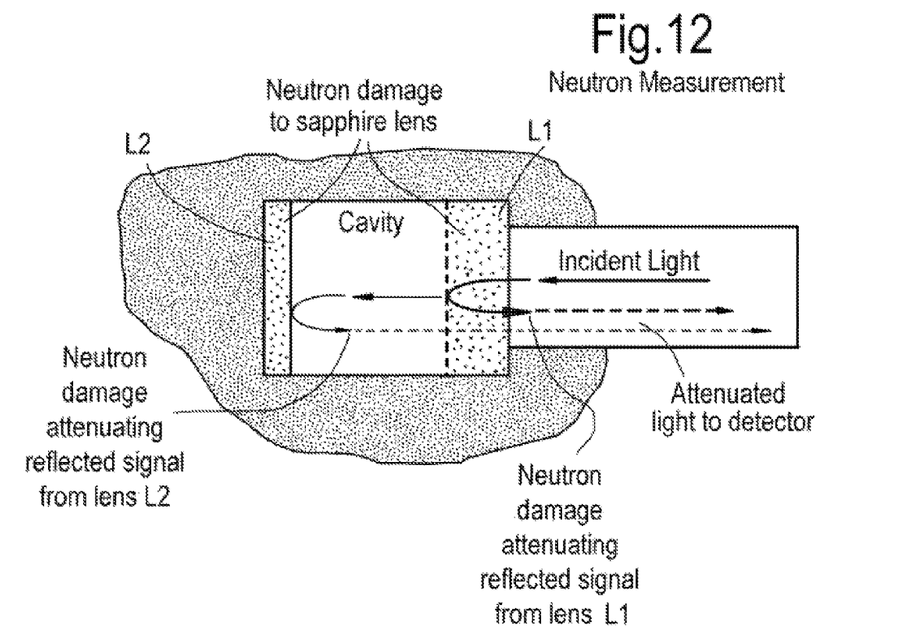
FIG. 12 shows schematically the attenuation of reflected light in the sensor of FIG. 9.

In the sensor of FIG. 9 attenuation of the reflected signal is thus related to the amount of stable point defects in the sapphire lattice of the lens L1, and to a lesser extent in the sapphire lattice of the lens L2. Attenuation of the reflected signal can be measured and monitored by a photo-multiplier, the amount of signal loss (attenuation) giving a measure of neutron fluence (dose). FIG. 12 shows schematically the attenuation of reflected light in the sensor of FIG. 9.

Attenuation of signal due to other factors generally also occurs, e.g. bend losses in the fibre optic cable. There are, however, fibre optic cables available which are resistant to bend losses. Also it is also possible to account for such losses by interrogating the fibre with light at two wavelengths (with no coherent interference). In this way bend loss in the fibre can be determined and subtracted from the overall attenuation measured by the sensor.

Figure 13:
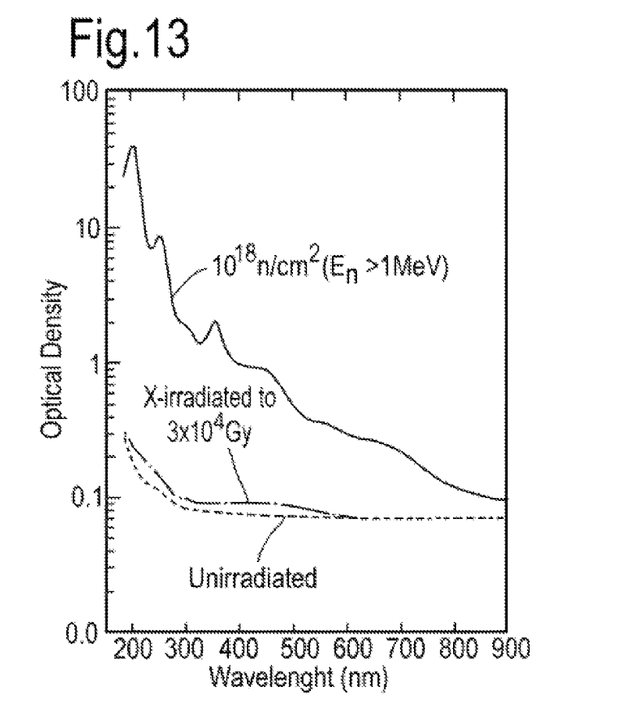
FIG. 13 shows the optical absorption spectra for irradiated and unirradiated sapphire as a function of wavelength.

FIG. 13 (taken from the Pells, Fudge, Murphy and Watt reference) shows the optical absorption spectra for irradiated and un-irradiated sapphire as a function of wavelength. Preferably, the sapphire in the sensor is interrogated at a wavelength of about 400 nm where a large difference exists between the irradiated and un-irradiated optical absorption. A plateau in the optical absorption of irradiated sapphire from about 380 to 450 nm wavelength as shown in FIG. 11 also helps to reduce uncertainty on these measurements.

Figure 14:
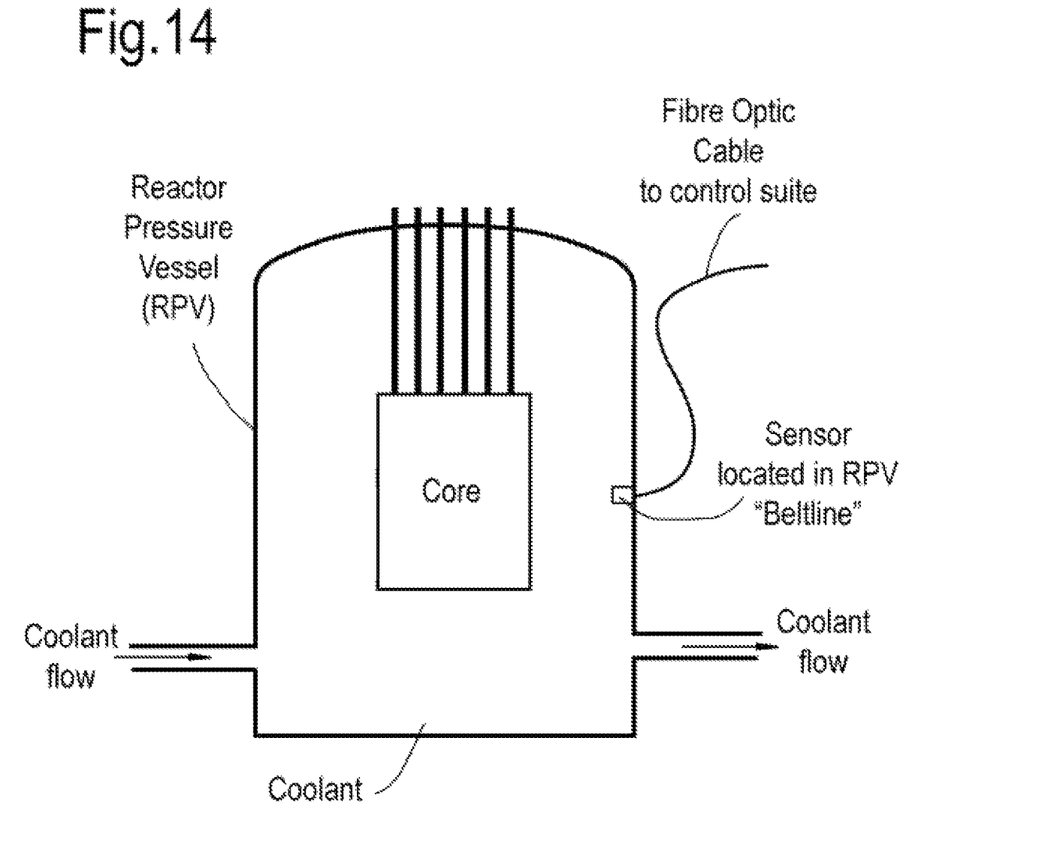
FIG. 14 shows schematically a nuclear reactor with a sensor of the type shown in FIG. 9 located at the RPV beltline region.

The combined temperature, pressure and neutron fluence sensor has applications in the nuclear industry. In particular, it would be of benefit in providing a large, reliable data set with which to validate materials models used to predict irradiation shift of pressure vessel materials and resultant safe operating procedures, remnant reactor life, plant life extension, etc. It could also partially or fully replace complex and costly dosimetery capsules. In general the area of most concern in a reactor is the area of the pressure vessel closest to the core (the "beltline" region). Thus a desirable position for the sensor would be in this region, as shown schematically in FIG. 14.

Other possible applications include uses in fuel transport flasks, reprocessing plants, fusion devices, nuclear instrumentation, instrumentation calibration, waste storage facilities, food irradiation facilities, materials test reactors, and nuclear core design validation experiments.

While the invention has been described in conjunction with the exemplary embodiments described above, many equivalent modifications and variations will be apparent to those skilled in the art when given this disclosure. For example, although FIG. 9 shows a combined temperature, pressure and neutron fluence sensor, in another sensor, only temperature or only pressure may be measured along with neutron fluence. Thus a combined temperature and neutron fluence sensor may not have the cavity and lens L2, and a combined pressure and neutron fluence sensor may be configured to reduce or minimise internal reflection within the lens L1 such that the lens L1 does not act as a Fabry-Pérot etalon. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A sensor for combined measurement of temperature, pressure and neutron fluence, the sensor comprising:
    a first optical body having at opposing, spaced sides an incident surface and a reflecting surface, and an optical pathway for carrying incident light to the incident surface, the first optical body acting as a Fabry-Pérot etalon, such that a portion of the incident light passes through the incident surface, reflects from the reflecting surface, and then returns along the optical pathway, wherein the first optical body is formed of a material whose optical absorbance increases depending on the neutron fluence experienced by the material, such that a corresponding characteristic attenuation is produced in the reflected light returned along the optical pathway depending on the neutron fluence experienced by the first optical body;
    a Fabry-Pérot interferometer having a cavity bounded on opposing sides by the reflected surface of the first optical body and a higher finesse mirrored surface of a second optical body, wherein a portion of the incident light passes through the first optical body, enters the cavity, reflects from the higher finesse mirrored surface, and then returns along the optical pathway;
    wherein varying the temperature of the first optical body leads to changes in the spacing between the incident and reflecting surfaces due to thermal expansion or contraction of the first optical body, such that corresponding temperature-sensitive characteristic changes are produced in the reflected light returned along the optical pathway; and,
    wherein at least one of the optical bodies is arranged such that it deforms under the influence of external pressure to vary the distance between the mirrored surfaces on the opposing sides of the cavity, leading to corresponding pressure-sensitive characteristic changes in the reflected light returned along the optical pathway.

2. A sensor according to claim 1, wherein the material whose optical absorbance increases depending on the neutron fluence experienced by the material is sapphire.

3. A sensor according to claim 1, further having a source of the incident light, the source being arranged to transmit the incident light along the optical pathway to the interferometer.

4. A sensor according to claim 3, wherein the source produces incident light having a wavelength in the range from 380 to 450 nm.

5. A sensor according to claim 1, further having a detector arranged to detect the reflected light returned along the optical pathway.

6. A sensor according to claim 5, further having a processor unit operatively connected to the detector for determining the neutron fluence experienced by the interferometer from the characteristic attenuation.

7. A sensor according to claim 6, further having a display and/or a memory device for respectively displaying and/or storing the determined neutron fluence.

8. A nuclear reactor pressure vessel fitted with one or more sensors according to claim 1.

9. A method comprising:
    measuring neutron fluence with the sensor according to claim 1.

* * * * *